United States Patent [19]

Stewart

[11] Patent Number: 4,826,685

[45] Date of Patent: May 2, 1989

[54] MOLLUSCICIDAL DEVICE

[75] Inventor: Ray F. Stewart, Redwood City, Calif.

[73] Assignee: Landec Labs, Inc., Redwood City, Calif.

[21] Appl. No.: 932,444

[22] Filed: Nov. 17, 1986

[51] Int. Cl.⁴ .................. A01N 25/08; A01M 1/20
[52] U.S. Cl. ..................... 424/410; 43/114; 43/131; 43/136; 424/84; 424/409; 514/481; 514/693
[58] Field of Search ............ 43/114, 136, 131; 424/405, 409, 419, 416, 407

[56] References Cited

U.S. PATENT DOCUMENTS

| | | | |
|---|---|---|---|
| 1,385,241 | 3/1974 | Grubb et al. | 424/14 |
| 2,938,830 | 5/1960 | Davey | 424/409 |
| 3,417,181 | 12/1968 | Cardarelli | 424/409 X |
| 4,007,258 | 2/1977 | Cohen et al. | 424/409 |
| 4,198,441 | 4/1980 | Young et al. | 43/136 X |
| 4,198,782 | 4/1980 | Kydonieus et al. | 424/419 X |
| 4,269,820 | 5/1981 | Davies et al. | 424/410 X |
| 4,320,113 | 3/1982 | Kydonieus | 424/416 |

FOREIGN PATENT DOCUMENTS

| | | | |
|---|---|---|---|
| 1180086 | 2/1970 | United Kingdom . | |
| 1240622 | 7/1971 | United Kingdom . | |
| 2074868 | 11/1981 | United Kingdom | 424/405 |
| 2080687 | 2/1982 | United Kingdom | 424/411 |
| 2115697 | 9/1983 | United Kingdom . | |
| 2119249 | 11/1983 | United Kingdom . | |

OTHER PUBLICATIONS

Chemical Patents Index, Basic Abstracts Journal, Section C, Week K04, Abstract No. 08680 K/04, Derwent Publications Ltd., London, GB; & JP-A-57 20300.
Chemical Abstracts, vol. 100, No. 11, 12th Mar. 1984, p. 170, Abstracts No. 81202a, Columbus, OH, U.S.; J. IGRC et al.
Chemical Abstracts, vol. 76, No. 9, Feb. 28th 1972, p. 101, Abstract No. 42732q. Columbus, OH, US: C. Mallet et al.

*Primary Examiner*—Thurman K. Page
*Attorney, Agent, or Firm*—Irell & Manella

[57] ABSTRACT

A molluscicidal device in the form of a chemophysical barrier which is placed in the path of molluscs (e.g., between their habitat and an area to be protected from infestation). The device comprises a solid body, typically in the form of a sheet or continuous length strip made of a thermoplastic water-insoluble polymer in which is dispersed a molluscicidal agent. The dimensions of the body, the nature of the agent, and the concentration of the agent on the surface of the body are such as to cause any mollusc that attempts to cross the body to be immobilized, whereby it remains on the body and receives a lethal dose of the agent.

20 Claims, No Drawings

MOLLUSCICIDAL DEVICE

DESCRIPTION

1. Technical Field

The invention is in the general field of pesticides. More particularly it relates to a molluscicidal device in the form of a molluscicidal agent-containing water-insoluble polymeric body that is placed in the path of molluscs. The body immobilizes any molluscs that attempt to traverse the body and transmits a lethal dose of the molluscicidal agent to the molluscs immobilized on the body.

2. Background

Various traps, baits and poisons have been used to control populations of land or aquatic molluscs. Metaldehyde, carbamates, and organophosphates are commonly used as molluscicides for land snails. Fudge, F. D, and Kuhr, R. J., *J Econ Entom*, (1972) 65:242–245. Organotin and copper compounds are commonly used to control aquatic snails, Japanese Pat. Publication No. 57-203003 teaches that saturated aliphatic alcohols such as ethanol and butanol or mixtures of ethanol and $C_8$ or $C_{10}$ alcohols are toxic to snails.

Several prior references describe polymer-based formulations of molluscicides, French Patent Publication No. 2,085,181 describes granules of the water-swellable polymer, polyvinylpyrrolidone, and metaldehyde. U.S. Pat. Nos. 3,417,181, 3,639,583, 3,851,053, 3,928,564, 4,012,221, and 4,228,614 describe formulations of organotin or insoluble copper compounds with polymeric binders that are useful as antifouling coatings for submerged marine structures and for the control of aquatic snails.

Insecticide-containing polymeric devices in the form of strips or collars have been used to control insects such as flies, roaches and fleas. Representative examples of such products are described in U.S. Pat. Nos. 3,318,769, 3,295,246, 3,705,938, 3,857,934, 3,864,468, and 4,320,113. None of these references mentions molluscicides and none of them describes a device that would be suitable as a toxic barrier to molluscs.

No prior art known to applicant teaches or suggests a molluscicidal device in the form of a solid body of a molluscicide in a water-insoluble thermoplastic polymer that has a relatively low surface concentration of molluscicide and acts as a chemophysical barrier to molluscs by immobilizing any mollusc that attempts to cross the body and transmitting a toxic dose of the molluscicide to themollusc while it is immobilized on the body.

DISCLOSURE OF THE INVENTION

One aspect of the invention is a molluscicidal device comprising a body adapted to be placed in the path of molluscs, said body being made of a water insoluble polymer having dispersed therein a molluscicidal agent, in which the concentration of the agent in the polymer and the permeability of the polymer to the agent are such that the body has a low surface concentration of the agent. whereby the body is resistant to rapid depletion of agent due to contact with environmental moisture, and the activity of the agent at said concentration and the smallest pathwise dimension of the body are sufficient to immobilize on the body molluscs that attempt to traverse the body, whereby such molluscs are retained in contact with the body for a sufficient time for them to receive a lethal dose of the agent from the body.

Another aspect of the invention is a molluscicidal composition comprising a mixture of:
(a) a low vapor pressure alcohol, and
(b) metaldehyde, a carbamate molluscicide, or a mixture of metaldehyde and a carbamate molluscicide.

MODES FOR CARRYING OUT THE INVENTION

The novel molluscicidal device of the invention provides a chemophysical barrier to molluscs that (1) is long lasting, (2) may be exposed to environmental moisture (rain, snow, fog, sprinklers, dew) without losing its efficacy (3) places a minimum amount of molluscicidal agent into the environment, (4) is not a danger to mammals such as children and pets, (5) is easy to position and reposition around the perimeter of plants or planting areas, and (6) can be manufactured in a form that is easy to store and handle.

A key feature of the molluscicidal device of the invention is that it is designed chemically and physically to immobilize molluscs that attempt to cross it. Prior devices that have involved the mechanism of pest immobilization have generally used adhesives to physically entrap the pest. These prior adhesive-based devices (e.g. fly paper) often do not employ pesticidal agents and rely solely on immobilization as a means of killing the pest. Use of an adhesive is not a feasible way to immobilize snails and slugs for several reasons. First, such molluscs do not adhere to conventional water-based adhesives because they secrete a slime that will not stick to such adhesives. Second, the device has to be exposed to environmental moisture which is likely to dissolve or otherwise degrade the adhesive. Finally, an adhesive-based device will pick up soil, leaves and other debris commonly found in the garden or other site of use.

Since the invention device is designed to immobilize the snail or slug on the device, it does not have to have a high surface concentration of molluscicidal agent. In this regard, prior nonadhesive based polymeric pesticidal devices, such as the cockroach strip described in U.S. Pat. No. 4,320,113, must have a high surface concentration of toxic agent so that the pest is killed as a result of a very short contact time with the device. Use of high surface concentrations is not feasible for long-lasting molluscicidal devices since the device must be exposed to rain, fog, dew and other environmental moisture which would wash the agent from the surface of the device. This would require the device to contain a large reservoir of molluscicide to be long-lived. Place more molluscicide residue in the environment than is necessary and pose a greater danger to mammals who might ingest the device or a portion of the device. With regard to mammalian safety, even if the invention device or a portion thereof is ingested, it is likely that the device or portion would be excreted before it released a harmful amount of the molluscicide.

Both the chemical composition and the structure of the invention device are important to its efficacy. In terms of chemical composition, the device is comprised of two basic components: (1) a thermoplastic or thermosetting water-insoluble polymer in which is dispersed (2) a molluscicidal agent. The concentration of the molluscicide in the polymer and the permeability of the polymer to the molluscicide at normal use temperatures are such that the concentration of molluscicide on the surface of the device is low, i.e., less than or equal to about 5 mg per square inch. Normally, the concentration of molluscicide on the surface of the device will be in the range of 0.1 to 5 mg per square inch. Preferably the surface concentration will be below about 1 mg per square inch. As indicated above, such low surface concentrations minimize the amount of toxic agent released to the environment and reduce the danger to mammals.

The polymer will normally be of the dense (nonporous), hydrophobic type rather than microporous type. In this regard, microporous polymers would tend to permit penetration of environmental moisture and leaching of the molluscicide from the device. Examples of thermoplastic polymers that may be use to form the device are: polyolefins such as polyethylene, polypropylene copolymers, ethylene-propylene copolymers, and ethylene-propylene-diene terpolymers; ethylene-vinyl acetate copolymers of about 5% to about 60% by weight vinyl acetate: poly(vinyl acetate) and other poly (vinyl esters); acrylic polymers such as acrylic and methacrylic ester polymers and copolymers, copolymers of alkyl or alkylene acrylates or methacrylates; copolymers of ethylene and alkyl acrylates; polybutadiene and butadiene copolymers such as butadiene-styrene-acrylonitrile polymers; polyesters such as polycapro lactone, poly(lactic acid), lactic acid-glycolic acid copolymers, polyamides such as nylon, polyalkylene oxides such as poly(propylene oxide) and poly(butylene oxide); polyurethanes: and cellulosics such as cellulose acetate, cellulose propionate, cellulose butyrate, cellulose acetate butyrate and cellulose acetate butyrate propionate. Blends of these polymers may be employed to obtain desired physical or chemical properties (e.g.. hydrolytic stability, hydrophobicity, softening point, viscosity and the like).

Examples of molluscicidal agents that may be used in the device are metaldehyde, N-naphthyl methylcarbamate, 4-(dimethylamino)-3,5-dimethyl phenol methylcarbamate, 3,5-dimethyl-4-(methylthio)phenol methylcarbamate, N-tritylmorpholine-5,2-dichloro-4-nitrosalicylanilide, and S-methyl-N-(methylcarbamoyl) oxythioacetimidate. In this regard, the term "carbamate molluscicide" as used herein is intended to include molluscicidal oxime carbamates and carbamates. Other suitable molluscicides are described by Fudge and Kuhr, supra. Mixtures of one or more of these molluscicides may be used. The molluscicide will usually comprise about 5% to 25% by weight of the polymer-molluscicide mixture. The polymer and molluscicide may be blended together using conventional polymer mixing equipment such as Henshel mixers, Banbury or Sigma mixers, and roll mills.

The polymer-molluscicide mixture may be formed into an appropriately shaped body by extrusion, casting, and the like. Alternatively, the mixture may be combined with liquid diluents as a solution, emulsion, or dispersion and be sprayed, painted, doctor-bladed, or otherwise applied to an appropriate substrate to provide the devices of the invention.

If the biological activity of a particular molluscicide is such that it is not capable of immobilizing molluscs, other molluscicides or agents that either enhance or directly cause immobilization may be added to the mixture. In this regard, it has been found that low (i.e.. less than 1 mm Hg at 25° C.) vapor pressure alcohols such as alkylene glycols and aliphatic alcohols of at least about 8 carbon atoms, and preferably 8 to 20 carbon atoms, enhance the ability of at least certain molluscicides to immobilize and/or kill molluscs. Such alcohols are generally not toxic to mammals and are typically used in cosmetics. The alcohol may be straight-chain or branched-chain. Examples of such alcohols are 2-ethylhexanol, n-octanol, decanol, undecanol, dodecanol, tetradecanol, pentdecanol, hexadecanol, and eicosanol. Many of these alcohols are sold commercially as mixtures. In addition to low vapor pressure alcohols, minor amounts of other materials such as antioxidants and UV stabilizers to help prevent degradation of the polymer, pigments to color the device or protect it from sunlight degradation, plasticizers to improve the processibility of the mixture, and dispersants and surfactants to facilitate the mixing of the polymer and molluscicide may optionally be included in the mixture.

The use of combinations of a low vapor alcohol and either metaldehyde, a carbamate molluscicide, or mixtures thereof is not limited to the chemophysical barriers described above. Such combinations may be used in conventional formulations such as in granules. wettable powders, and sprayable liquids (solutions, emulsions, suspensions). The weight ratio of alcohol to metaldehyde/carbamate in such combinations (both in the chemophysical barrier and in other formulations) will usually be in the range of about 1:5 to 5:1, more usually about 1:1 to 2:1. The conventional formulations will include a suitable diluent (solid in the case of solid formulations, liquid in the case of liquid formulations) and other conventional additives, depending upon the particular formulation, such as baits, binders, colorants, surfactants, and the like.

A key functional feature of the physical structure of the body is that it be (1) shaped so that it may be placed in the path of molluscs to provide an effective barrier between the mollusc habitat and the area to be protected from infestation, and (2) sized so that the smallest pathwise dimension of the body is sufficient to expose any mollusc attempting to cross the body to an immobilizing amount of the biologically active agent(s) present on the surface of the body. Typically the body will be shaped as a sheet or continuous strip whose smallest pathwise dimension (width in the case of a continuous length strip) is less than about one-third of a meter and normally less than about one-ninth of a meter. In functional terms, the smallest pathwise dimension of the body must be at least equal to the "immobilization length" of the body—the immobilization length being the distance over which a mollusc must travel on the body for it to receive a dose of the active ingredient(s) that causes it to lose the ability to move in a normal fashion. This length is a function of the immobilization activity and surface concentration of the molluscicide. The snail or slug will thus be immobilized while in contact with the body and remain in contact with the body for a time sufficient to receive (presumably via absorption) a lethal dose of the active ingredient(s) on the surface of the body. From this discussion it is apparent that the toxicity of the device is a function of the surface toxicity of the body and the time spent on the surface of the body by the mollusc. Immobilization is accomplished at low surface concentrations of active ingredient(s) by including in the body a molluscicide that is known to effectively immobilize slugs and snails, a nerve toxin, or a low vapor pressure alcohol as described above. In this regard, the mode of action of such alcohols is not known and may be due to a toxic or immobilizing activity of the alcohol itself, an absorption promoting activity of the alcohol, or a combination of these mechanisms. Reserve toxin/immobilizing agent within the polymer matrix continuously diffuse(s) to the surface to replace materials that are removed from the surface by molluscs, environmental moisture, debris, or the like.

When the body is made in the form of a continuous strip it may be desirable to coat one side of the strip with an adhesive so that the device can be readily affixed to plant stems, plant containers, walkways defining planting areas and the like. Strip forms of the device may be easily laid in place about the perimeter of the area to be protected from mollusc infestation and moved, if necessary or desirable, to other locations. Further, they may be tied about the stems of plants to protect foliage from mollusc attack. Continuous strip forms of the device are conveniently made in the form of rolls from which the user may unravel lengths necessary to protect a given area.

The invention is further illustrated by the following examples. These examples are not intended to limit the invention in any manner.

FORMULATION

All ingredients used in making the devices described in the examples were purchased from commercial sources. The ingredients were blended in a Brabender in the indicated proportions (proportions are specified in weight %, unless indicated otherwise). After blendlng the mixtures were pressed into 6 in×6 in slabs 35 to 45 mils thick.

TEST PROCEDURE

European brown snails (Helix Aspera Muller) were collected and kept in an empty terrarium prior to use. Test slabs of the molluscicidal, polymeric formulations were rinsed with tap water and blotted dry prior to use. A snail was placed at the center of the slab and observed. The distance traveled by the snail after placement on the slab was recorded and is referred to as the immobilization length (I.L.). After a snail was immobilized (or moved a total of 12 in) it was transferred to a clean box for observation. Mortalities were determined after 24, 48 and 72 hr. All tests were done in triplicate and immobilization lengths were averaged.

GENERAL EFFICACY TESTS

Various formulations of polymers and molluscides were formulated and tested for efficacy.

The results of these tests are reported in Table 1 below.

TABLE 1

| Formulation | A | B | C | D | E | F | G | H |
|---|---|---|---|---|---|---|---|---|
| Elvax 250[1] | 80 | — | — | 89 | 90 | 70 | 70 | 66 |
| Poly caprolactone | — | — | 93 | — | — | — | — | — |
| Polyvinyl acetate | — | 93 | — | — | — | — | — | — |
| Decanol | — | — | — | — | 10 | — | 10 | 10 |
| Metaldehyde | 10 | 7 | 7 | — | — | 10 | 10 | 10 |
| Sevin[2] | — | — | — | 5 | — | — | — | 2 |
| Carbon black | 10 | — | — | 5 | | 10 | 10 | 10 |
| Nonionic surfactant | — | — | — | 1 | | 10 | — | 2 |
| Immobilization Length (inches) | >8 | >12 | >12 | >12 | >12 | >8 | 3.8 | 1.5 |
| 24-hour mortality | 0/3 | 0/3 | 0/3 | 0/3 | 0/3 | 1/3 | 3/3 | 4/4 |
| 48-hour mortality | 0/3 | 0/3 | 0/3 | 0/3 | 0/3 | 1/3 | — | — |

[1]ethylene-vinyl acetate copolymers, 28 wt % vinyl acetate
[2]N—naphthyl methylcarbamate As reported the formulas containing only metalaldehyde (A, B, C), Sevin (D) and decanol (E) as active ingredients provided no or marginal (F) mortality in these tests. The presence of nonionic surfactant in formulas D and F had no apparent effect as a toxin or as an enhancer. In comparison the formulas that contained either or both of Sevin and metaldehyde in combination with decanol (G and H) provided 100% mortality after 24 hr. Further the immobilization length associated with formulations G and H was dramatically less than with formulations A–F.

VARIATION OF POLYMER, CARBAMATE, AND ALCOHOL

The following formulation was prepared:

Two part urethane:

elastomer (Conap EN-2): 87.5%

Lannate (oxime carbamate)[1]: 4.4%

Metaldehyde: 5.8%

2-ethyl hexanol: 2.3%

[1]S-methyl-N-(methylcarbamoyl) oxythioacetimidate

The material was mixed thoroughly and degassed to remove entrapped air, then coated into a thin sheet of polyethylene. The material was cured at 50° C. for 1 hr followed by 6 hr at room temperature.

Efficacy testing was carried our as above with the following result:

IL=1 inch 24 hr mortality=$\frac{2}{4}$

Typically a reactive system (e.g., two part urethane) such as this would be coated onto a carrier substrate, for example, a fabric backing, a cardboard or paper material, or other suitable carrier. The system could be used without a backing if desired. A reactive system such as this could be used as a paint if desired to provide a field-applied barrier.

Similar systems could be readily prepared from various latex or emulsion systems. Typically these are water-based systems. Such systems must be water resistant once dried.

PRODUCT LONGEVITY TESTS

The following formulation of ethylene-vinyl acetate copolymer, Sevin, metaldehyde and decanol was prepared as described above.

| Component | Wt % |
|---|---|
| Elvax 250 | 64 |
| metaldehyde | 12 |
| Statex 160[1] | 10 |
| Sevin | 2 |
| Decanol | 10 |
| piperonyl butoxide | 1 |
| Tween 20[2] | 1 |

[1]Carbon black
[2]Nonionic surfactant

Two 6 in×6 in×0.035 in slabs were pressed from the formulation. A 0.05 in thick film of polyethylene was laminated to each side of one of the slabs (designated slab A). The two slabs were fastened to a board and placed outdoors. Snails were placed on the slabs periodically and tested for immobilization and mortality at 48 hr as above. The results of these tests are reported in Table 2 below.

TABLE 2

| Immobilization Length (mortality) | Slab A | B |
|---|---|---|
| Day 1 | 4 in. (2/2) | <1 in. (3/3) |
| Day 6 | 3.3 in. (2/3) | <1 in. (2/2) |
| Day 92 | 1.5 in. (2/2) | 1.5 in. (2/2) |

As reported in Table 2 these formulations continued to provide 100% mortality even after exposure to the elements for approximately three months.

IMMOBILIZATION AND SURFACE CONCENTRATION STUDIES

The formulation used in the product longevity tests reported above was used in these studies.

Immediately after preparation, this material exhibited an immobilization length of <1 inch and a toxicity of 4/4 in 24 hours when snails were left on the material subsequent to becoming immobile. No surface excess of material was observed.

After a period of 8 months storage, a thin film was observed on the surface of the material. Immobilization was again tested and found to be <1 inch. Three snails were placed on the slab for five minutes (during which time they showed complete immobilization) and then placed in a vented plastic container for observation. After 24 hours the mortality was 0/3.

Another slab of aged material was lightly washed with warm soapy water. It was found that 5.5 mg/square inch of surface material was removed. This material was now tested and the immobilization length was 2 inches. Three snails were placed on the plaque for 5 minutes (during which time complete immobilization was observed) and then removed for observation as before. After 24 hours the mortality was 0/3 and all snails had become mobile.

Four snails were then placed on the washed plaque (immobilization length of 1 inch) and left for observation. After 24 hours no snails had moved off of the plaque and the mortality was 4/4.

The data is shown in Table 3.

TABLE 3

| | Effect of Surface concentration and Immobilization | | | |
|---|---|---|---|---|
| Test | Surface Concentration | Exposure Time | I.L. | 24-hour Mortality |
| A | Freshly prep. | 24 hr | <1 in. | 4/4 |
| A | 5 mg/in sq | 5 min | <1 in. | 0/3 |

TABLE 3-continued

| | Effect of Surface concentration and Immobilization | | | |
|---|---|---|---|---|
| Test | Surface Concentration | Exposure Time | I.L. | 24-hour Mortality |
| B | 0 mg/in sq* | 5 min | 2 in. | 0/3 |
| C | 0 mg/in sq* | 24 hr | 2 in. | 4/4 |

*The concentration of surface excess was below the level of detection for the procedure used, indicating that it was less than 0.5 mg/in sq.

This set of experiments shows that a high surface concentration is not needed to kill snails. It also shows that immobilization is an important aspect of the efficacy of the device.

FORMULATIONS WITHOUT ALCOHOL

The following formulations were made, formed into slabs and tested as above.

| A | | B | |
|---|---|---|---|
| Elvax 250 | 90% | Elvax 250 | 80% |
| metaldehyde | 5 | caffeine | 10 |
| Sevin | 5 | Sevin | 10 |
| | | Nopacol 4-L | 0.1[1] |

[1]Nonionic surfactant

Formulation A provided an immobilization length of 3-6 in and a 24 hr mortality of 3/5, whereas formulation B had an immobilization length of 1 in and a 24 mortality of 3/3. These results show that effective formulations may be made that lack a long-chain aliphatic alcohol. They further indicate that caffeine is either itself a molluscicide or it enhances the activity of carbamate molluscicides.

SPRAYABLE FORMULATIONS CONTAINING ALCOHOLS

Several water-based systems were prepared containing alcohols and/or carbamate or oxime carbamate molluscicides. Small amounts of these formulations were then sprayed into 5 in×3 in plastic containers. The containers were allowed to stand open for 30 min and then several snails were placed inside and vented lids put on top. After a period of time T the containers were rinsed with clean water and the snails were observed for 72 hours.

Formulations and results follow:

| Formulation | 1 | 2 | 3 | 4 | 4 | 5 | 6 | 7 | 8 |
|---|---|---|---|---|---|---|---|---|---|
| Ethanol | 2% | | | | | | | | |
| Isopropanol | | | 2% | | | | | | |
| Decanol | | 1.5% | | | | 1% | 1% | | 1% |
| Sevin[1] | | | | 1% | 1% | 1% | 1% | | |
| Lannate | | | | | | | | 0.5% | 0.5% |
| Nopacol 4-0 | | 0.3% | | | | | | 0.5% | 0.5% |
| Volume (ml) | 1 | 1 | 1 | 0.5 | 1 | 1 | 0.5 | 0.6 | 0.6 |
| Time T (min) | 120 | 120 | 120 | 90 | 90 | 90 | 90 | 90 | 90 |
| Mortality (24 hr) | 0/4 | 1/7 | 0/3 | 1/4 | 2/6 | 8/9 | 3/4 | 1/4 | 3/3 |

[1]Sevin was in the form of a 15% commercial solution.

The above results show that none of the alcohols tested is an effective molluscicide when used in a low concentration spray. Also, the data clearly show that the carbamates and oxime carbamates tested are not effective as low concentration sprays (combined mortality=4/13). Combinations of low vapor pressure alcohols and carbamates or oxime carbamates are. however, very effective (combined mortality=14/16).

Modifications of the above-described modes for carrying out the invention that are obvious to those of skill in the field of pesticide formulation are intended to be within the scope of the following claims.

I claim:

1. A molluscicidal device that acts as a chemophysical barrier to terrestrial molluscs and kills terrestrial molluscs through prolonged physical contact rather than by releasing a molluscicidal agent into the environment inhabited by the molluscs comprising a body in the form of a sheet or strip adapted to be placed in the path of terrestrial molluscs, said body being made of a water insoluble polymer having dispersed therein a terrestrial molluscicidal agent, in which the concentration of the agent in the polymer and the permeability of the polymer to the agent are such that the body has a low surface concentration of the agent, whereby the body is resistant to rapid depletion of agent due to contact with environmental moisture, and the activity of the agent at said concentration and the smallest pathwise dimension of the sheet or strip are sufficient to immobilize on the body terrestrial molluscs that attempt to traverse the body, whereby such molluscs are retained in contact with the body for a suffcient time for them to receive a lethal dose of the agent from the body.

2. The device of claim 1 wherein the agent is a combination of a carbamate molluscicide and caffeine.

3. The device of claim 2 wherein the carbamate molluscicide is N-naphthyl methylcarbamate.

4. The device of claim 1 wherein said dimension is less than about one-third of a meter.

5. The device of claim 1 wherein said dimension is less than about one-sixth of a meter.

6. The device of claim 1 wherein the agent is a combination of materials exhibiting biological activity against molluscs, at least one of the materials having the ability to immobilize molluscs.

7. The device of claim 6 wherein the combination of materials comprises metaldehyde and a carbamate molluscicide.

8. The device of claim 7 wherein the carbamate molluscicide is N-naphthyl methylcarbamate.

9. The device of claim 1 wherein the body includes a material that enhances the ability of the agent to immobilize molluscs and/or the toxicity of the agent to molluscs.

10. The device of claim 6 wherein the agent is a combination of an alcohol having a vapor pressure of less than 1 mm Hg at 25° C. and either metaldehyde, a carbamate molluscicide or mixtures of metaldehyde and a carbamate molluscicide.

11. The device of claim 10 wherein the alcohol is a aliphatic alcohol of at least about 8 carbon atoms.

12. The device of claim 11 wherein the alcohol is decanol.

13. The device of claim 10 wherein the carbamate molluscicide is N-naphthyl methylcarbamate.

14. The device of claim 1 wherein the surface concentration of the agent is less than about 5 mg/square inch.

15. A molluscicidal composition comprising a mixture of:
(a) an alcohol of at least about 8 carbon atoms having a vapor pressure of less than 1 mm Hg at 25° C., and
(b) metaldehyde, a carbamate molluscicide, or a mixture of metaldehyde and a carbamate molluscicide.

16. The moluscicidal composition of claim 15 wherein the weight ratio of (a) to (b) is in the range of about 1:5 and 5:1.

17. The molluscicidal composition of claim 15 wherein the alcohol is an aliphatic alcohol.

18. The molluscicidal composition of claim 15 wherein the carbamate molluscicide is N-naphthyl methylcarbamate.

19. The molluscicidal composition of claim 15 wherein the composition is in the form of a sprayable liquid.

20. The molluscicidal composition of claim 15 wherein the composition is in a solid particulate form.

* * * * *